US006489446B1

(12) United States Patent
Rothstein et al.

(10) Patent No.: US 6,489,446 B1
(45) Date of Patent: *Dec. 3, 2002

(54) SELF-ALIGNING PEPTIDES MODELED ON HUMAN ELASTIN AND OTHER FIBROUS PROTEINS

(75) Inventors: Aser Rothstein, Toronto (CA); Fred Keeley, Toronto (CA); Steven Rothstein, Clive, IA (US)

(73) Assignees: HSC Research and Development Limited Partnership, Toronto (CA); Protein Specialties, Ltd., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/340,736

(22) Filed: Jun. 29, 1999

Related U.S. Application Data

(63) Continuation-in-part of application No. 08/911,364, filed on Aug. 7, 1997, now Pat. No. 5,969,106.
(60) Provisional application No. 60/023,522, filed on Aug. 7, 1996.

(51) Int. Cl.[7] .............................. A61K 38/00; A61F 2/06
(52) U.S. Cl. ........................ 530/353; 530/324; 530/329; 530/330; 530/350; 514/2; 514/12; 514/17; 514/18; 435/69.1; 435/69.7; 424/192.1; 424/193.1; 424/194.1; 623/1.1; 623/11; 623/12
(58) Field of Search ................................. 530/353, 324, 530/329, 330, 350; 514/2, 12, 17, 18, 21; 435/69.1, 69.7; 424/192.1, 193.1, 194.1; 623/1, 11, 12

(56) References Cited

U.S. PATENT DOCUMENTS

| | | | |
|---|---|---|---|
| 4,132,746 A | 1/1979 | Urry et al. | 260/857 |
| 4,179,333 A | 12/1979 | Braeumer et al. | 435/60 |
| 4,327,078 A | 4/1982 | Charlet et al. | 424/45 |
| 4,419,288 A | 12/1983 | Cioca | 260/123.7 |
| 4,474,763 A | 10/1984 | Lubowe | 424/177 |
| 4,474,851 A | 10/1984 | Urry | 428/373 |
| 4,589,882 A | 5/1986 | Urry | 623/11 |
| 4,659,740 A | 4/1987 | Usher | 514/773 |
| 4,776,853 A | 10/1988 | Klement et al. | 8/94.11 |
| 4,783,523 A | 11/1988 | Urry et al. | 550/323 |
| 4,870,055 A | 9/1989 | Urry et al. | 514/12 |
| 4,960,423 A | 10/1990 | Smith | 623/1 |
| 4,963,656 A | 10/1990 | Mitani | 530/353 |
| 4,979,959 A | 12/1990 | Guire | 623/66 |
| 5,223,420 A | 6/1993 | Rabaud et al. | 424/425 |
| 5,243,038 A | 9/1993 | Ferrari et al. | 536/23.1 |
| 5,250,516 A | 10/1993 | Urry | 514/17 |
| 5,336,256 A | 8/1994 | Urry et al. | 623/1 |
| 5,416,074 A | 5/1995 | Rabaud et al. | 514/21 |
| 5,519,004 A | 5/1996 | Urry | 514/7 |
| 5,527,610 A | 6/1996 | Urry | 428/373 |
| 5,969,106 A * | 10/1999 | Rothstein et al. | 530/353 |

FOREIGN PATENT DOCUMENTS

| | | |
|---|---|---|
| EP | 0 329 622 A | 8/1989 |
| WO | WO 88/03533 | 5/1988 |
| WO | WO 90/05177 | 5/1990 |
| WO | WO 91/16919 | 11/1991 |
| WO | WO 92/09695 | 6/1992 |
| WO | WO 94/14958 | 7/1994 |
| WO | WO 95/24478 | 9/1995 |
| WO | WO 98/05685 | 2/1998 |

OTHER PUBLICATIONS

Zena Indik et al., "Alternative Splicing of Human Elastin mRNA Indicated by Sequence Analysis of Cloned Genomic and Complementary DNA", Aug. 1987, pp. 5680–5684, vol. 84.
G.M. Bressan et al., "Relevance of Aggregation Properties of Tropoelastin to the Assembly and Structure of Elastic Fibers", 1986, pp. 209–216.
Stavros J. Hamodrakas et al., "Structural and Functional Features of Drosophila chorion proteins s36 and and s38 from Analysis of Primary Structure and Infrared Spectroscopy", Oct. 1989, pp. 307–313, vol. 11.
Robson et al., *J. Biol. Chem*, vol., 268, pp.–1440–1447.
Cappello, "Protein Engineering For Biomaterials Applications," Curr. Opinion Struct. Biol., 2:582–86 (1992).
Alexandra H. Simmons et al., "Molecular Orientation and Two–Component Nature of the Crystalline Fraction of Spider Dragline Silk", Jan. 5, 1996, vol. 271.
Debra Bedell–Hogan et al. "Oxidation, Cross–linking and Insolubilization of Recombinant Tropoelastin by Purified Lysyl Oxidase", May 15, 1993, pp. 10345–10350, vol. 268.
Aleksander Hinek et al., "67–kD Elastin–binding Protein Is a Protective "Companion" of Extracellular Insoluble Elastin and Intracellular Tropoelatin", Jul. 1994, pp. 563–574.
Zena Indik et al., "Production of Recombinant Human Tropoelastin: Characterization and Demonstration of Immunologic and Chemotactic Activity", Jul. 1990, pp. 80–86, vol. 280.
Paul Robson et al, "Characterization of Lamprin, an Unusual Matrix Protein form Lamprey Cartilage", Jan. 15, 1993, pp. 1440–1447, vol. 266.
A. H. Tamburro, et al. "On The Structure And Elesticity Of Elastin", *Advances In Life Sciences* 115–27 (1990).
Aleksander Hinek "Nature and The Multiple Functions Of The 67–kD Elastin–/Laminin Binding Protein", *Cell Adhesion & Comm.* 2: 185–93 (1994).
S. Dutoya et al., *"Unexpected Original Property of Elastin Derived Proteins: Spontaneous Tight Coupling With Natural and Synthetic Polymers,"* Biomaterials 19 (1998) 147–155.

* cited by examiner

Primary Examiner—Karen Cochrane Carlson
Assistant Examiner—Abdel A. Mohamed
(74) *Attorney, Agent, or Firm*—Foley & Lardner

(57) ABSTRACT

A polypeptide is provided that has a secondary structure characterized by at least three beta-sheet/beta-turn structures, and that is not a naturally occurring fibrous protein. Such polypeptides, illustrated by one modeled on elastin, are useful in prosthesis.

13 Claims, 6 Drawing Sheets

FIG. 1A

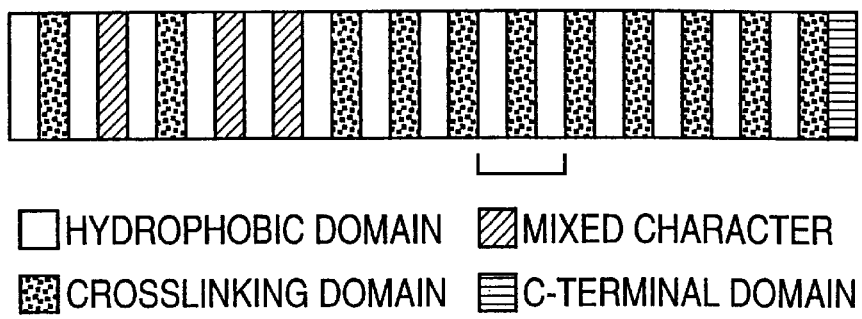

☐ HYDROPHOBIC DOMAIN   ▨ MIXED CHARACTER
▦ CROSSLINKING DOMAIN   ☰ C-TERMINAL DOMAIN

FIG. 1B

```
       1          11         21         31         41         51
GGVPGAIPGG VPGGVFYPGA GLGALGGGAL GPGGKPLKPV PGGLAGAGLG AGLGAFPAVT
FPGALVPGGV ADAAAAYKAA KAGAGLGGVP GVGGLGVSAG AVVPQPGAGV KPGKVPGVGL
PGVYPGGVLP GARFPGVGVL PGVPTGAGVK PKAPGVGGAF AGIPGVGPFG GPQPGVPLGY
PIKAPKLPGG YGLPYTTGKL PYGYGPGGVA GAAGKAGYPT GTGVGPQAAA AAAAKAAAKF
GAGAAGVLPG VGGAGVPGVP GAIPGIGGIA GVGTPAAAAA AAAAAKAAKY GAAAGLVPGG
PGFGPGVVGV PGAGVPGVGV PGAGIPVVPG AGIPGAAVPG VVSPEAAAKA AAKAAKYGAR
PGVGVGGIPT YGVGAGGFPG FGVGVGGIPG VAGVPSVGGV PGVGGVPGVG ISPFAQAAAA
AKAAKYGVGT PAAAAAKAAA KAAQFGLVPG VGVAPGVGVA PGVGVAPGVG LAPGVGVAPG
VGVAPGVGVA PGIGPGGVAA AAKSAAKVAA KAQLRAAAGL GAGIPGLGVG VGVPGLGVGA
GVPGLGVGAG VPGFGAGADE GVRRSLSPEL REGDPSSSQH LPSTPSSPRV PGALAAAKAA
KYGAAVPGVL GGLGALGGVG IPGGVVGAG PAAAAAAAKAA AKAAQFGLVG AAGLGGLGVG
GLGVPGVGGL GGIPPAAAAK AAKYGAAGL GGVLGGAGQFP LGGVAARPGF GLSPIFPGGA
CLGKACGRKR K
```

FIG. 1C

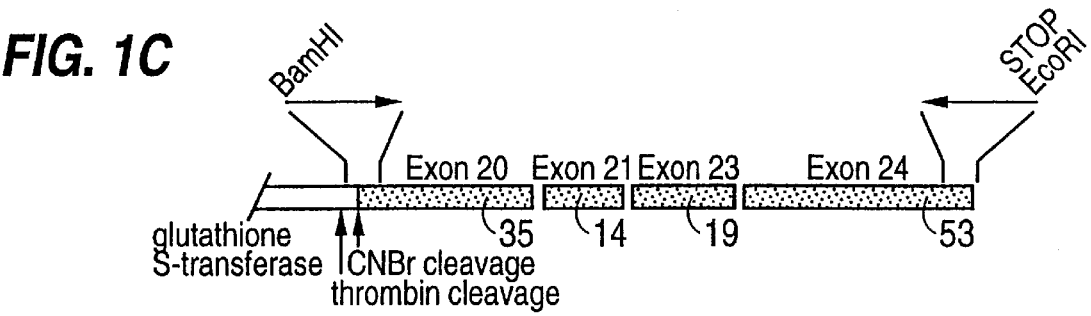

FIG. 1D

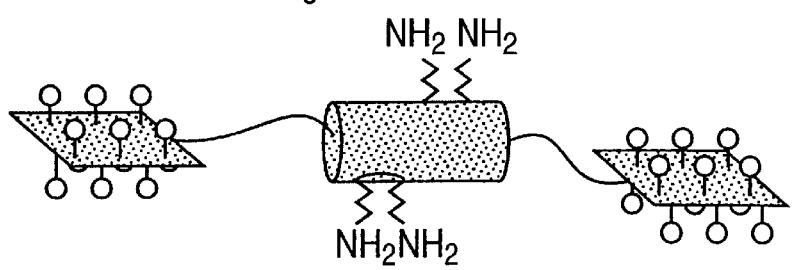

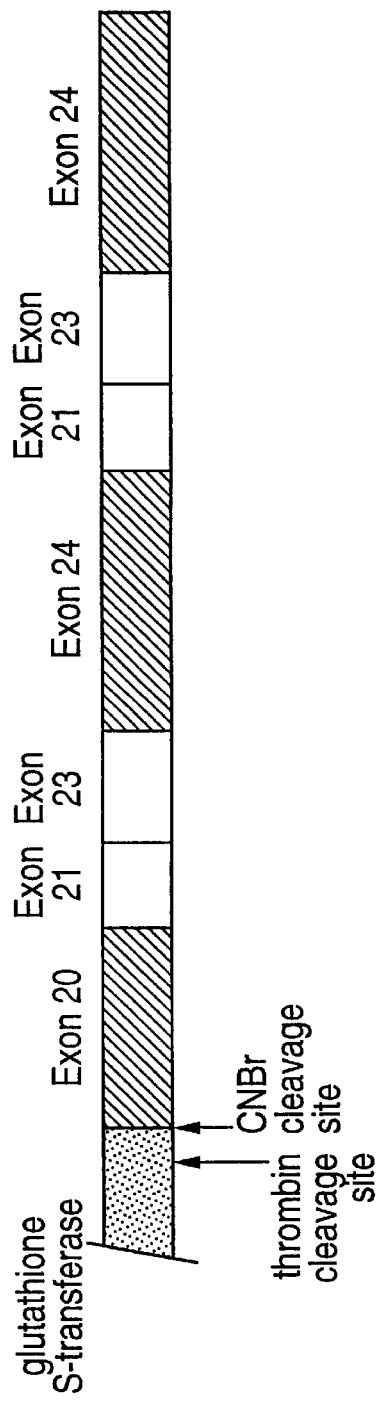
*FIG. 4A*
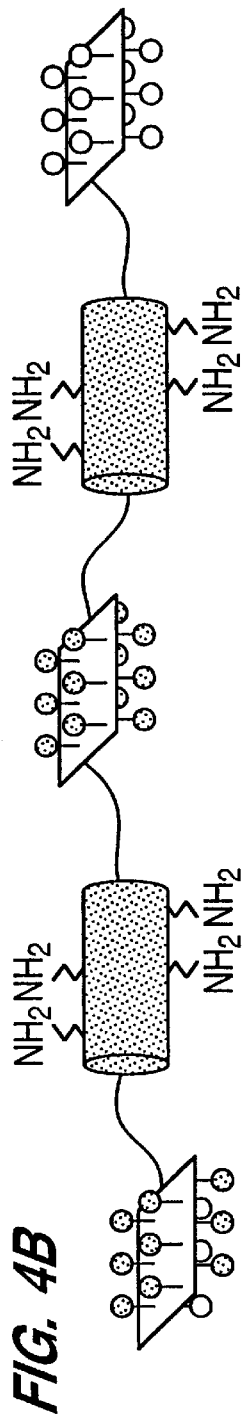
*FIG. 4B*
*FIG. 4C*
FPGFGVGVGG IPGVAGVPGV GGVPGVGGVP GVGISPEAQA AAAAKAAKYG
VGTPAAAAAK AAAKAAQFGL VPGVGVAPGV GVAPGVGVAP GVGLAPGVGV
APGVGVAPGV GVAPAIGP E AQAAAAAKAA KYGVGTPAAA AAKAAAKAAQ
FGLVPGVGVA PGVGVAPGVG VAPGVGLAPG VGVAPGVGVA PGVGVAPAIG P

FIGURE 5A

| | | | |
|---|---|---|---|
| PGFGVGVGGI | PGVAGVPGVG | GVPGVGGVPG | VGISPEAQAA |
| AAAKAAKYGV | GTPAAAAAKA | AAKAAQFGLV | PGVGVAPGVG |
| VAPGVGVAPG | VGLAPGVGVA | PGVGVAPGVG | VAPAIGP |

FIGURE 5B

| | | | |
|---|---|---|---|
| FPGFGVGVGG | IPGVAGVPGV | GGVPGVGGVP | GVGISPEAQA |
| AAAAKAAKYG | VGTPAAAAAK | AAAKAAQFGL | VPGVGVAPGV |
| GVAPGVGVAP | GVGLAPGVGV | APGVGVAPGV | GVAPAIGP |

FIGURE 5C

| | | | |
|---|---|---|---|
| PGFGVGVGGI | PGVAGVPGVG | GVPGVGGVPG | VGISPEAQAA |
| AAAKAAKYGV | GTPAAAAAKA | AAKAAQFGLV | PGVGVAPGVG |
| VAPGVGVAPG | VGLAPGVGVA | PGVGVAPGVG | VAPAIGPEAQ |
| AAAAKAAKY | GVGTPAAAAA | KAAAKAAQFG | LVPGVGVAPG |
| VGVAPGVGVA | PGVGLAPGVG | VAPGVGVAPG | VGVAPAIGP |

SELF-ALIGNING PEPTIDES MODELED ON HUMAN ELASTIN AND OTHER FIBROUS PROTEINS

RELATED APPLICATIONS

This application is a continuation-in-part of U.S. patent application Ser. No. 08/911,364, filed Aug. 7, 1997, now U.S. Pat. No. 5,969,106, which is based on U.S. provisional patent application serial No. 60/023,522, filed Aug. 7, 1996. The entire contents of both of these applications, including their specifications, claims and drawings, are incorporated herein by reference in their entirety.

BACKGROUND OF THE INVENTION

The present invention relates to self-aligning peptides modeled on human elastin and other fibrous proteins. The peptides are useful, for example, as biocompatible material for implantation into humans, or for elastic materials.

Currently available synthetic implant materials for soft tissue prosthesis fall short of optimal biocompatibility. The ideal material would provide appropriate structural support, would be biocompatible, in the sense of causing no immunogenic or thrombogenic response, would mimic the physical properties of the tissue replaced, and would provide a friendly environment for normal cell infiltration and growth.

While tissue can sometimes be borrowed from another part of the patient's body, such as by skin grafting or blood vessel replacement, this approach has several limitations, including the limited availability of appropriate donor tissue. Synthetic materials such as dacron, teflon (Gortex) and polyurethane, as well as metals (such as stainless steel and titanium), often are used for prostheses of soft tissues. While these materials can meet the requirements of strength, durability, and flexibility, as foreign materials they are not maximally biocompatible for long term use.

One approach to dealing with this problem has been to coat non-biological materials with proteins or other natural substances. Another approach has been to use biological materials from animal tissue preparations. For example, animal skin preparations have been used to cover burns, and processed animal blood vessels have been used to provide potential blood vessel replacements for humans.

Elastin, a natural structural protein, has received considerable attention for potential use in prostheses, both in soluble forms for coating non-biological prostheses, and in solid forms to produce biologically-derived prostheses. Elastin has structural properties which make it suitable for use in prosthesis and it provides a biocompatible, non-thrombogenic surface for cell infiltration. It is a durable, extremely stable, and highly insoluble extracellular matrix protein which imparts the properties of extensibility and elastic recoil to tissues in which it is found, including large blood vessels, elastic ligaments, lung parenchyma, and skin.

Large arteries are a good source of elastin. Because human arteries are not available in quantity, however, animal arteries have been the primary source of elastin. Because arterial elastin is a highly insoluble matrix, soluble elastin-derived material is generated by treating the insoluble protein with acid or alkali, producing hydrolyzates such as alpha- and kappa-elastin. These are relatively undefined mixtures of peptides of mixed sizes.

In attempts to develop biocompatible materials, soluble animal elastin materials have been used to coat non-biological prosthetic materials, usually with fixation by chemical cross-linking agents. For example, U.S. Pat. No. 4,960,423 (Smith) is directed to a synthetic vascular prosthesis coated with a water-soluble peptide derived from animal elastin.

U.S. Pat. No. 5,416,074 (Rabaud) is directed to a composition comprising elastin or a solubilized elastin peptide and another connective tissue protein, such as fibrin. The solubilized elastin peptide has a molecular weight of greater than 10,000.

U.S. Pat. No. 4,474,851 (Urry) is directed to an elastomeric composite material comprising an artificial core fiber, such as Dacron, and a polypeptide comprising repeating tetrapeptide or pentapeptide units. The units are derived from units observed to be repeated in the tropoelastin molecule, Val-Pro-Gly-Val-Gly (VPGVG) (SEQ ID NO:6), and Val-Pro-Gly-Gly (SEQ ID NO:7)(VPGG). The polypeptide comprises a series of beta-turns and is proposed to have a beta-coil structure. The polypeptide provides elastomeric properties to the composite material, but has little structural strength or integrity. The artificial core fiber provides these latter properties to the composite material.

U.S. Pat. No. 4,979,959 (Guire) is directed to a method of improving the biocompatibility of solid biomaterials by coating them with biocompatible agents and chemically linking the biocompatible agents to the surface via a photochemical reaction.

Elastin-based materials also have been used to produce solid materials from which prostheses can be manufactured. These include soluble animal elastin co-aggregated with other proteins such as collagen, fibrin, fibronectin and laminin, to produce gel-like materials, and polymerized materials derived from short hydrophobic sequences of human elastin (SEQ ID NO:5)(such as PGVGVA). In some cases, these synthetic peptides also include short alanine-rich sequences containing lysine residues, allowing cross-linking between the elastin-like peptides or to other proteins such as collagen. Both elastin and collagen contain crosslinks derived from lysine. For example, U.S. Pat. No. 5,223,420 (Rabaud) is directed to an elastin-based product comprising an adduct containing elastin and at least one other protein, such as fibrin.

U.S. Pat. No. 4,589,882 (Urry) is directed to an artificial elastomeric copolymer comprising an elastomeric component of repeating units of tetrapeptides and pentapeptides and a crosslinking component which may comprise amino acid residues. The repeating units are derived from elastin. U.S. Pat. No. 4,132,746 (Urry) is directed to a synthetic, insoluble, crosslinked polypentapeptide. The pentapeptide is the VPGVG (SEQ ID NO:6) peptide present in tropoelastin. See also U.S. Pat. No. 4,500,700, U.S. Pat. No. 4,870,055, and U.S. Pat. No. 5,250,516 (all to Urry) for other materials derived from this peptide. The polypeptides described in these patents comprise a series of beta-turns and are proposed to have a beta-coil structure.

Animal arteries also have been stripped of extraneous material, leaving largely a matrix of elastin and collagen in tubular form that can be used for blood vessel replacement. For example, U.S. Pat. No. 4,776,853 (Klement) is directed towards a process for preparing an implantable biological material from suitable donor tissue.

The respective contents of the above-described patents and publications are incorporated by reference herein in their entirety.

The materials discussed above were developed to satisfy the need for prostheses suitable for implantation into humans. These materials are not completely satisfactory, however, and there remains a need for prosthesis which have appropriate mechanical properties and which can be used in contact with blood, tissue fluids and cells without adverse effects.

SUMMARY OF THE INVENTION

It is an object of the present invention, therefore, to provide a material that can be used in prostheses that are implanted into humans. It is another object of the invention to provide prostheses suitable for implantation into humans.

In accordance with these and other objects, the invention provides a polypeptide that comprises at least three beta-sheet/beta-turn structures and that is not a naturally occurring fibrous protein. In accordance with one embodiment, the polypeptide consists essentially of a portion of the amino acid sequence set forth in FIG. 1B. In accordance with another embodiment, the polypeptide consists essentially of a portion of the amino acid sequence of an animal elastin. In accordance with yet another embodiment, the polypeptide consists essentially of a portion of the amino acid sequence of lamprin. In accordance with another embodiment, the polypeptide consists essentially of a portion of the amino acid sequence of a spider silk protein.

The invention also provides a material suitable for implantation into humans, wherein the material consists essentially of a polypeptide consisting essentially of a portion of the amino acid sequence set forth in FIG. 1B. In accordance with another embodiment, the invention provides a prosthesis comprising an animal material, wherein a surface of the animal material is coated with a polypeptide consisting essentially of a portion of the amino acid sequence set forth in FIG. 1B. In accordance with another embodiment, the invention provides a prosthesis comprising a synthetic material, wherein a surface of the synthetic material is coated with a polypeptide consisting essentially of a portion of the amino acid sequence set forth in FIG. 1B. In accordance with yet another embodiment, the invention provides a prosthesis comprising a metal, wherein a surface of the metal is coated with a polypeptide consisting essentially of a portion of the amino acid sequence set forth in FIG. 1B.

The invention also provides a cosmetic material comprising a polypeptide consisting essentially of a portion of the amino acid sequence set forth in FIG. 1B.

The invention also provides elastic material and high tensile-strength material comprising a polypeptide that comprises at least three beta-sheet/beta-turn structures and that is not a naturally occurring fibrous protein.

The invention also provides a material comprising two or more polypeptides selected from the group consisting of (A) a polypeptide consisting essentially of a portion of the amino acid sequence set forth in FIG. 1B comprising at least three beta-sheet/beta-turn structures; (B) a polypeptide consisting essentially of a portion of the amino acid sequence of an animal elastin comprising at least three beta-sheet/beta-turn structures; (C) a polypeptide consisting essentially of a portion of the amino acid sequence of lamprin comprising at least three beta-sheet/beta-turn structures; and (D) a polypeptide consisting essentially of a portion of the amino acid sequence of a spider silk protein comprising at least three beta-sheet/beta-turn structures, wherein the two or more polypeptides may be the same or different.

The invention also provides a polypeptide having the primary structure of a portion of a naturally occurring fibrous protein and a secondary structure comprising at least three beta-sheet/beta-turn structures, wherein (A) each of the beta-sheet/beta-turn structures comprises from 3 to about 7 amino acid residues and (B) the polypeptide is not a naturally occurring fibrous protein.

Additional objects and advantages of the invention are set forth in part in the description that follows, and in part will be obvious from the description, or may be learned by practice of the invention. The objects and advantages may be realized and obtained by means of the invention recited in the appended claims.

BRIEF DESCRIPTION OF THE FIGURES

FIG. 4A shows the GST fusion construct used to express the polypeptide of the present invention named MFU-2.

FIG. 4B is a cartoon representation of the hydrophobic and crosslinking domains of MFU-2.

FIG. 4C shows the amino acid sequence of MFU-2 (SEQ ID NO:2).

FIGS. 5A, 5B and 5C show the amino acid sequences of MFU-3 (SEQ ID NO:9), MFU-4 (SEQ ID NO:10), and MFU-5 (SEQ ID NO:11), respectively.

DETAILED DESCRIPTION OF PREFERRED EMBODIMENTS

Figure 1:
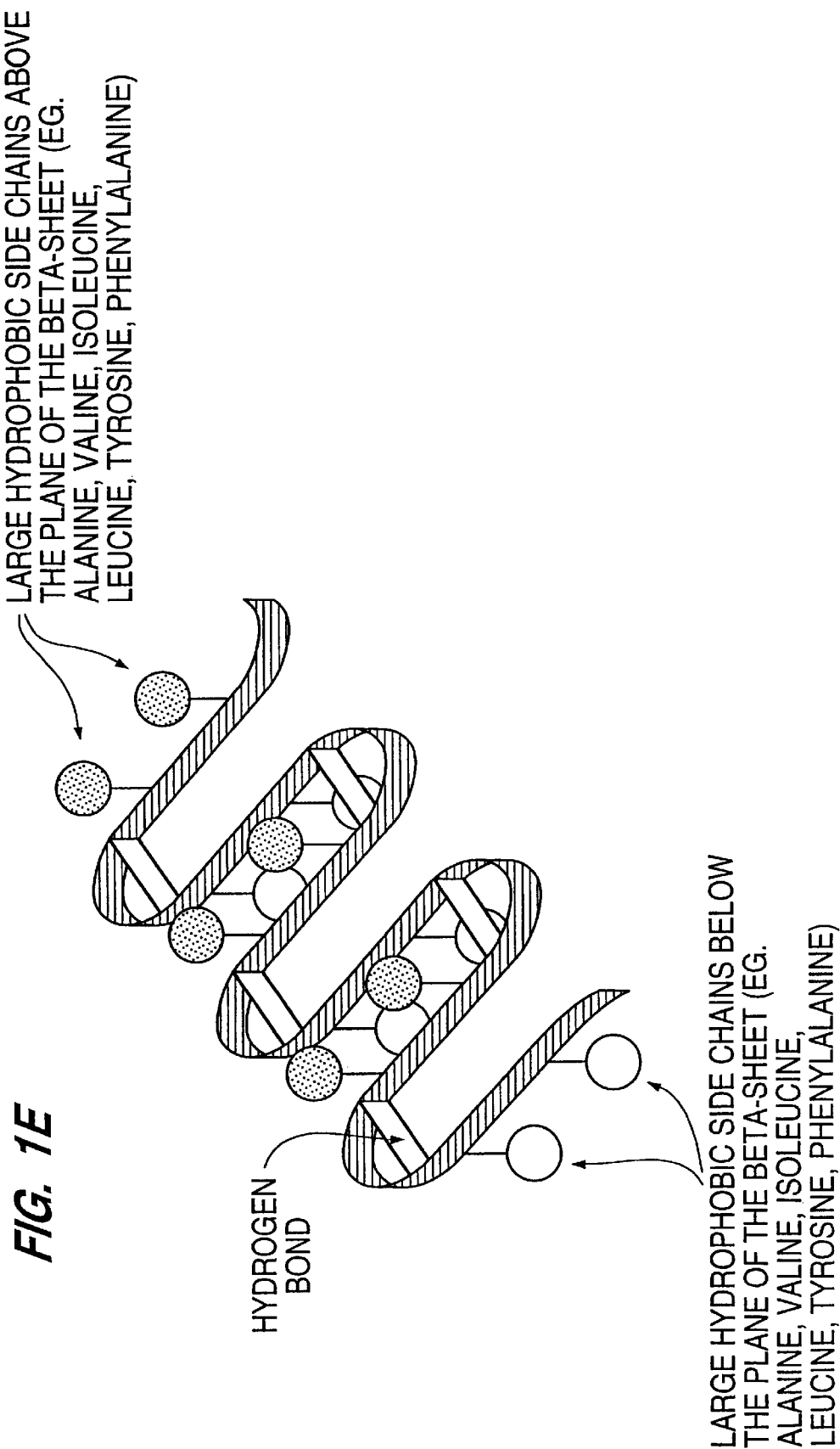
FIG. 1A shows the domain structure of human elastin. The location of the domains used in the expressed construct described in Example 2 is indicated by the bracketed region.
FIG. 1B shows the amino acid sequence of human elastin (SEQ ID NO:1), without the signal peptide. The underlined amino acid residues comprise the polypeptide of the present invention named MFU-1.
FIG. 1C shows the GST fusion construct used to express MFU-1.
FIG. 1D is a cartoon representation of the hydrophobic and crosslinking domains corresponding to the expressed exons described in Example 1.
FIG. 1E is a schematic diagram of a peptide with beta-sheet/beta-turn structures.

The present invention is directed to unique polypeptides modeled on human elastin and other naturally occurring fibrous proteins. While the discussion below often refers to human elastin as the exemplary parent protein, polypeptides modeled on other naturally occurring fibrous proteins are contemplated by the present invention, and can be made and used in manners analogous to those described for polypeptides modeled on human elastin.

The phrase "parent protein" here denotes the protein on which a polypeptide of the invention is modeled. For example, a polypeptide modeled on human elastin comprises a portion of the human tropoelastin amino acid sequence. A "naturally occurring fibrous protein" is any fibrous protein found in nature, where the phrase "fibrous protein" has the conventional meaning in the art. Thus, a fibrous protein is a protein that consists of polypeptide chains arranged in a matrix so as to form long fibers or sheets. See Lehninger, BIOCHEMISTRY 60 (1975). Examples of fibrous proteins include, but are not limited to, elastin, lamprin and spider silk protein. Robson et al., *J. Biol. Chem.* 268: 1440–47 (1993), incorporated by reference herein in its entirety, discloses additional proteins on which polypeptides of the present invention may be modeled.

Amino acid sequence information is available for elastin and other fibrous extracellular matrix proteins, such as spider silks and lamprin. Together with analyses of secondary and tertiary structures, this information has led to general theories concerning their mechanical properties and, in particular, mechanisms for their assembly into insoluble fibers.

Elastin is synthesized in vivo as a monomer called tropoelastin which, upon secretion from the cell, assembles into a branched polymeric network through the formation of covalent crosslinks called desmosines. Mecham et al., in CELL BIOLOGY OF EXTRACELLULAR MATRIX, 2D ED. (New York, 1991). Desmosine crosslinks are generated enzymically through the action of lysyl oxidase. Each desmosine incorporates the side chains of four lysine residues, two from each of the polypeptide chains involved. Although the principles underlying the elastomeric properties of elastin remain a matter of debate, there is agreement that this unusual property is dependent on the strongly hydrophobic nature of the protein.

Tropoelastin consists predominantly of alternating hydrophobic and crosslinking domains. Indik et al., Proc. Nat'l Acad. Sci. USA 84: 5680–84 (1986). Crosslinking domains are rich in alanine (A), with the lysines (K) destined for involvement in crosslink formation present in KAAK (SEQ ID NO:3) and KAAAK spacings (SEQ ID NO:4). The domains separating these crosslinking regions are strongly hydrophobic in character, and contain many tandemly repeated penta- and hexa-peptide sequences. In human elastin the most striking of these is the sequence (SEQ ID NO:5) PGVGVA, repeated 7 times in exon 24. Indik et al., supra.

Structural studies on repeat hydrophobic sequences indicate an exclusively beta-sheet/beta turn structure. That is, they comprise beta-sheets with intervening beta-turns. Analogous beta-sheet/beta-turn structures also contribute to the structures of other self-aggregating, polymeric matrix proteins, including spider silks, lamprin, and silk moth chorion, all of which form stable fibers or matrices with high tensile strength. These structures have been proposed to be crucial for the ability of these proteins to self-assemble. Robson et al., supra.

There is evidence that the periodically spaced hydrophobic domains direct the assembly of tropoelastin into higher order structures. Tropoelastin, as well as solubilized fragments of elastin (i.e., kappa-elastin and alpha-elastin), and synthetic peptides corresponding to the hydrophobic repeat sequences can all undergo coacervation, a process in which hydrophobic interactions between polypeptide chains result in the formation of oligomeric, fibrillar structures. This self-aggregation is not random: the hydrophobic domains facilitate the alignment of tropoelastin monomers for crosslinking into the fibrillar elastic matrix. Robson et al., supra; Bressan et al., J. Ultrastr. & Mol. Struct. Res. 94: 209–16 (1986).

As shown in FIG. 1A, human elastin consists for most of its length of alternating crosslinking domains and hydrophobic domains. The crosslinking domains consist mainly of lysine (K) and alanine (A) residues in KAAK (SEQ ID NO:3) and KAAAK (SEQ ID NO:4) sequences, wherein the lysine residues are in a suitable conformation for oxidative deamination by lysyl oxidase and subsequent formation of the covalent desmosine crosslinks. Indik et al., supra. The hydrophobic domains are rich in hydrophobic pentapeptide and hexapeptide sequences believed to be in beta-sheet/beta-turn structures. Tamburro et al., ADVANCES IN LIFE SCIENCES 115–27 (1990). These hydrophobic regions are believed to be important to elastin's physical properties of extensibility and elastic recoil, and to the ability of tropoelastin (the monomeric precursor of elastin) to self-aggregate into fibrillar structures. Robson et al., supra; Tamburro et al., supra. Other proteins capable of self-aggregation and self-alignment into stable fibrillar matrices, including eggshell chorion proteins of insects, spider dragline silk, and lamprin from lamprey cartilage, all possess similar regions of hydrophobic repeat peptides with beta-sheet/beta-turn structures. Hamodrakas et al., Int. J. Biol. Macromol. 11: 307–13 (1989); Simmons et al., Science 271: 84–87 (1996); Robson et al., supra.

The polypeptides of the present invention are modeled on elastin and other fibrous proteins, such as spider silk and lamprin, and comprise the number and kinds of amino acid residues necessary for self-alignment, which is a first step in fiber formation. For convenience, each polypeptide of the present invention is referred to as a minimal functional unit, or MFU. The secondary structure of an MFU according to the present invention comprises at least three beta-sheet/beta-turn structures.

As discussed above, beta-sheet and beta-turn structures are well known in the art. Beta-sheet structures in accordance with the present invention are typically comprised of several amino acid residues, for example, from 3 to about 7 amino acid residues, acceptably from about 5 to about 7 amino acid residues, and, in particular, from 5 to 7 amino acid residues. The amino acid residues of the beta-sheet structures may have hydrophobic side chains. Beta-turn structures in accordance with the present invention are typically initiated by two amino acid residues, often GG or PG, and may comprise additional amino acid residues. For example, a beta-turn structure in accordance with the present invention may comprise from about 2 to about 4 amino acid residues, acceptably from 2 to 4 amino acid residues, and, in particular, four amino acid residues.

FIG. 1E is a schematic diagram of a peptide with beta-sheet/beta-turn structures. The shaded ribbon represents a peptide. The six straight portions of the ribbon represent the beta-sheet structures and the five curved portions of the ribbon represent the beta-turn structures. The empty circles represent hydrophobic side chains which are directed below the beta-sheets, and the shaded circles represent hydrophobic side chains which are directed above the beta-sheets. These hydrophobic side chains are on amino acid residues such as alanine, valine, isoleucine, leucine, tyrosine and phenylalanine. The rectangles indicate hydrogen bonds which stabilize the beta-turn structures. See also Robson et al., supra; Lehninger, supra, at pages 133–35.

The MFUs of the present invention are soluble, and exhibit the property of coacervation, aligning themselves in the same manner as the parent protein. For example, the hydrophobic sequences of the MFUs align in the same manner as the hydrophobic sequences of the parent proteins. When considering the secondary structure of the MFUs, this means that the beta-sheets of the MFUs are aligned with each other. This alignment occurs in the same manner as in the parent proteins, with the beta-sheets being stacked in a "lego"-type motif. See Robson, et al., supra. In elastin-derived MFUs, the alignment also results in the lysine residues aligning in a manner that permits crosslinking between the MFUs.

One embodiment of the present invention provides a polypeptide having the primary structure (that is, the amino acid sequence) of a portion of a naturally occurring fibrous protein and a secondary structure comprising at least three beta-sheet/beta-turn structures, wherein the polypeptide is not a naturally occurring fibrous protein. Preferably, each of the beta-sheet/beta-turn structures comprises from 3 to about 7 amino acid residues. The polypeptide is long enough to identify the parent protein to which it corresponds. It is believed that a length of at least about 10 amino acid residues is sufficient in this regard. The polypeptide may be longer and, for example, can be up to the length of the entire parent protein.

Also contemplated as part of the present invention is a polypeptide comprising the primary structure of a portion of a naturally occurring fibrous protein wherein the primary structure is modified by the addition, substitution and/or deletion of one or more amino acid residues. The polypeptide has a secondary structure comprising at least three beta-sheet/beta-turn structures and exhibits the properties of self-alignment described herein. While there is no set limit on the number of modifications that could be made, it is believed that modifications involving the addition, substitution and/or deletion of from 1 to about 20, particularly from 1 to about 10, specifically from 1 to about 5, amino acid residues can be effected while maintaining the above-described properties of the polypeptide.

Preferably, only conservative amino acid alterations are undertaken. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

For example, modifications in the hydrophobic regions of the polypeptide may comprise substituting one or more of the amino acids residues at the beta-turns with other amino acids that initiate beta-turns. For example, one or more of the P or G residues may be replaced with a G or P residue, respectively, or may be replaced with a serine residue. Additionally or alternatively, modifications may be made to the amino acid residues in the beta-sheet structure, such as the addition, deletion or substitution of one or more amino acid residues. For example, an amino acid residue having a hydrophobic side chain can be replaced by a different amino acid residue having a hydrophobic side chain, or having a side chain with similar properties. Exemplary substitutions include intersubstitutions of alanine, valine, isoleucine, leucine, tyrosine and phenylalanine.

For polypeptides comprising a crosslinking domain, any number of additions, substitutions and deletions can be made that do not interfere with the alpha-helical structure of the crosslinking domain, such as additions, deletions, and conservative amino acid substitutions, as discussed above. Also, lysine residues can be replaced with any other amino acid residue that participates in crosslinking, such as acidic or basic residues, including arginine, aspartic acid and glutamic acid.

In accordance with one embodiment of the invention, a polypeptide is provided whose amino acid sequence is a variant of a portion of the amino acid sequence set forth in FIG. 1B. The amino acid sequence of such a polypeptide corresponds to a portion of the amino acid sequence set forth in FIG. 1B, wherein the amino acid sequence set forth in the Figure is modified by the addition, deletion, or substitution of from 1 to about 10 amino acid residues. Such a polypeptide has a secondary structure comprising at least three beta-sheet/beta-turn structures and exhibits the properties of self-alignment described herein. In accordance with another embodiment of the invention, a polypeptide is provided whose amino acid sequence is a variant of the amino acid sequence set forth in FIG. 4C. The amino acid sequence of such a polypeptide corresponds to a portion of the amino acid sequence set forth in FIG. 4C, wherein the amino acid sequence set forth in the Figure is modified by the addition, deletion, or substitution of from 1 to about 10 amino acid residues, for example, from 1 to about 5 amino acid residues. Such a polypeptide has a secondary structure comprising at least three beta-sheet/beta-turn structures and exhibits the properties of self-alignment described herein. Polypeptides whose amino acid sequences are variants of the amino acid sequences set forth in FIGS. 5A–5C (SEQ ID NOS:9, 10, and 11) also are encompassed by the present invention. The amino acid sequences of such polypeptides comprise a portion of an amino acid sequence set forth in FIGS. 5A, 5B or 5C (SEQ ID NOS:9, 10, and 11), wherein the amino acid sequence set forth in the Figure is modified by the addition, deletion or substitution of from 1 to about 10 amino acid residues, for example, from 1 to about 5 amino acid residues. Such polypeptides have a secondary structure comprising at least three beta-sheet/beta-turn structures and exhibit the properties of self-alignment discussed herein.

While the description below uses MFUs modeled on elastin as exemplary MFUs, peptides derived from other proteins are encompassed by the present invention. For example, peptides derived from any other fiber-forming proteins, including spider silk and lamprin, are contemplated as part of the present invention. These MFUs can be obtained as described herein for MFUs modeled on elastin. Moreover, mixtures of MFUs from different parent proteins (e.g., MFUs modeled on lamprin and elastin) can be used together to produce a variety of materials.

The domain structure of human elastin is illustrated in FIG. 1A. As shown in this Figure, there are a number of alternating crosslinking and hydrophobic domains. The hydrophobic domains each are believed to comprise a number of beta-sheet/beta-turn-forming sequences. These domains represent probable MFUs of elastin. One of these, used in further experimentation, is designated by the bracket and is named MFU-1 (see Example 1 below). FIG. 1B sets forth the amino acid sequence of human elastin. The underlined amino acid residues, residues 374–499, comprise MFU-1. Other MFUs modeled on human elastin include polypeptides comprising amino acid residues 19–160, 188–367 and 607–717, respectively. The amino acid sequence of MFU-3 (SEQ ID NO: 9; FIG. 5A) corresponds to that of MFU-1 without the first five amino acid residues. The amino acid sequence of MFU-4 (SEQ ID NO:10; FIG. 5B) corresponds to that of MFU-1 without the first four amino acid residues.

MFUs modeled on human elastin comprise a portion of the amino acid sequence of the tropoelastin molecule (FIG. 1B) and have at least three beta-sheet/beta-turn structures in their secondary structure. They also may comprise amino acids residues which are capable of participating in crosslinking, such as lysine residues. In one embodiment of the invention, the MFU comprises two amino acid residues capable of participating in crosslinking in such a manner as to form a desmosine-type linkage. For example, the MFU may comprise a KAAK SEQ ID NO:3 or KAAAK SEQ ID NO:4 amino acid sequence.

In a preferred embodiment, a polypeptide modeled on human elastin consists essentially of a portion of the amino acid sequence set forth in FIG. 1B. The phrase "A consists essentially of B" herein denotes that A comprises B and possibly other components that do not materially affect the characteristics of the A-B material. For example, a polypeptide consisting essentially of a portion of the amino acid sequence set forth in FIG. 1B denotes a polypeptide which comprises a portion of the amino acid sequence set forth in FIG. 1B and which also may comprise other amino acid residues that do not materially alter the characteristics of the polypeptide. That is, the polypeptide maintains the characteristics of having at least three beta-sheet/beta-turn structures, and self-aligning in the same manner as tropoelastin peptides.

As described above, the secondary (beta-sheet/beta-turn) structure of the MFUs is believed to guide the self-aggregation and self-alignment of the MFUs such that the MFUs align themselves in a manner that mimics the structure of aggregates of the parent protein. For example, the beta-sheets of the MFUs are aligned, and the lysine residues of elastin-modeled MFUs are aligned for enzymic or chemical crosslinking into stable polymeric structures, mimicking the way tropoelastin monomers form the elastin protein.

An MFU can be obtained by any method, including direct synthesis or recombinant production of the peptide. For example, the DNA for an MFU modeled on human elastin can be obtained directly from DNA coding for human elastin either by cleavage of the DNA and selection of the appropriate segment, or by synthesis of the DNA via a variety of well-known methods.

By means of available technology, DNA sequences coding for tandem repeats of any human elastin MFU, or for MFUs containing larger domains of human elastin, up to and including the entire tropoelastin molecule, can be constructed. These larger elastin sequences may offer advantages in terms of their kinetics of assembly or their mechanical properties. For example, MFU-2, which consists of exons 20, 21, 23, 24, 21, 23, and 24 of human elastin, has been expressed and purified. The amino acid sequence of this peptide is set forth in FIG. 4C. MFU-2 demonstrates an increased tendency towards spontaneous self-aggregation than MFU-1, as evidenced by a lower coacervation temperature. See Example 6 below. The amino acid sequence of MFU-5 (SEQ ID NO:11; FIG. 5C) corresponds to that of MFU-2 without the first amino acid residue.

While the MFUs of the present invention are normally soluble in solution, simple manipulations of pH, salt content and temperature of these solutions initiate coacervation and self-alignment of the polypeptides, resulting in aggregates of elastin-like fibers. The exact conditions that will bring about coacervation and self-alignment of the MFUs varies depending on the MFU polypeptide and the MFU solution to be manipulated. Conditions that bring about coacervation are well-known to those skilled in the art, and those skilled in the art can induce coacervation and self-alignment of MFUs by following routine laboratory procedures.

Figure 3:
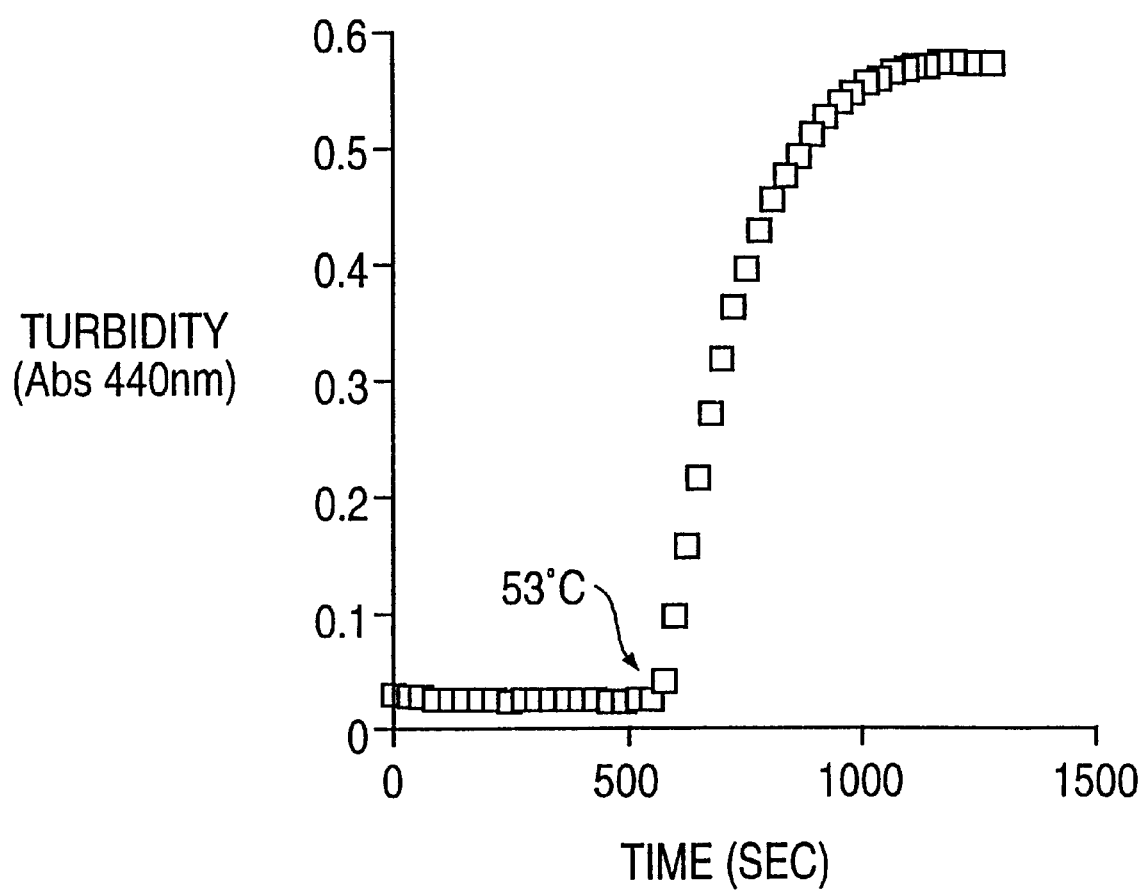
FIG. 3 illustrates the coacervation (self-aggregation) of MFU-1.

FIG. 3 illustrates the ability of the MFUs of the present invention to coacervate. In particular, FIG. 3 illustrates the coacervation (self-aggregation) of MFU-1 of human elastin. The peptide was dissolved at a concentration of 0.25 mg/ml in phosphate-buffered saline, pH 7.4, containing 1.5M NaCl and 0.3 mM $CaCl_2$, and the temperature of the solution was raised at a uniform rate. The onset of coacervation occurred at 53° C., and is indicated by an increase in turbidity of the solution. The data set forth in Example 4 below illustrate the ability of MFUs to assemble with non-human elastin.

A characteristic property of the MFUs of the present invention is their ability to self-assemble in an ordered manner, in the same manner as the tropoelastin monomers of human elastin. For example, the MFUs align themselves in an order that aligns their beta-sheet structures and that permits crosslinking between the individual MFU peptides, when the polypeptide is modeled on elastin. This process of self-alignment and self-aggregation is considered to be the first step in fiber formation. After enzymic crosslinking, the fibers can be made into a material that has chemical and structural properties similar to those of natural elastin polymers. This MFU material can be used to construct human elastin-like prostheses such as tubes for blood vessel replacement and sheets for other uses such as wound or burn healing. Alternatively, the MFUs can be co-aggregated with other proteins, for example collagen, to provide prosthesis material that resembles the natural structural materials of the body.

MFU-based material is subject to infiltration of cells growing in the patient, including endothelial cells, and the prosthesis can become a permanent, living, tissue replacement. This human-like MFU material is more biocompatible than other elastin-containing materials which have heretofore been proposed for prostheses, including the polymers produced from chemically synthesized sequences of elastin described in the Urry patents and the material produced from hydrolyzed non-human elastin co-aggregated with other proteins described above.

An MFU modeled on human elastin in accordance with the present invention offers distinct advantages over other elastin preparations. For example, in contrast to the solubilized fragments of elastin used before, an MFU is a single peptide of defined composition. The MFU is considerably smaller than the parent protein and simpler in structure, and therefore is easier to produce or express in quantity, to handle in solution, and to manipulate for experimental and practical purposes. Like other elastin preparations, the MFU is non-thrombogenic and provides a friendly environment for cell infiltration. In addition, being composed entirely of a human elastin sequence, an MFU is non-immunogenic, thus providing a truly biocompatible material.

MFUs modeled on human elastin according to the present invention also can be used in any way that human or animal elastin is used. For example, the soluble MFUs of human elastin of the present invention can be used to coat the surfaces of non-biological materials, such as prosthesis, in the same manner that solubilized (i.e., hydrolyzed) non-human elastin preparations, such as animal alpha- and kappa-elastins, have been used. MFUs can be used to coat any prosthesis, including a prosthesis comprising a synthetic material, an animal materials, and/or a metal. The prostheses can be coated with many layers of MFUs. For example, from 1 layer to 500 or more layers of MFU can be coated onto a prosthesis. The MFUs can be crosslinked after being coated onto the prosthesis to improve the permanence of the coating. As used herein, the term prosthesis is meant to encompass any material that is implanted into the body, including material for blood vessel replacement, for heart valve replacement for tissue replacement (i.e., "filler" material implanted after tissue loss), cloth-like material, stents, and materials for use as coverings for burns or wounds to promote healing.

Because the MFU's of the present invention are non-thrombogenic, and provide a surface on which endothelial and other cells can adhere and grow, prostheses coated with MFUs are more biocompatible than an uncoated prosthesis. Coating synthetic prosthesis with MFUs modeled on human elastin significantly inhibits platelet binding and activation. Moreover, prostheses coated with MFUs have the advantage over prosthesis coated with animal-derived elastin of containing a human sequence and, hence, being non-immunogenic. Also, the MFUs comprise a defined, homogeneous peptide rather than an undefined mixture of peptides of various sizes, like the animal-derived products previously described.

The MFUs of human elastin of the present invention also can be used in cosmetics, for example, in the manner that hydrolyzed animal elastin are used. See U.S. Pat. No. 4,179,333 (Braeumer), U.S. Pat. No. 4,659,740 (Usher), U.S. Pat. No. 4,474,763 (Lubowe), U.S. Pat. No. 4,419,288 (Cioca), U.S. Pat. No. 4,327,078 (Charlet) and U.S. Pat. No. 4,963,656 (Mitani), the respective contents of which are incorporated herein by reference in their entirety.

The MFUs of the present invention can be used in conjunction with animal elastin and collagen frameworks, as a human blood vessel replacement. The animal elastin/collagen material is obtained by extracting all other proteins, cellular and soluble components from animal blood vessels, leaving a tube consisting essentially of animal elastin and collagen. See, for example, U.S. Pat. No. 4,776,853 (Klement), discussed above. The MFUs spontaneously associate with the animal elastin matrix of animal vessel preparations because of their inherent property of self-assembly and self-alignment. The entire surface of animal elastin vessels can therefore be covered with multiple layers of human elastin MFUs, with permanent association achieved by enzymic or chemical crosslinking. Animal vessels with a human MFU surface will have substantially decreased immunogenicity and improved biocompatibility over non-coated animal elastin prostheses.

As discussed above, solubilized (hydrolyzed) animal elastin has been co-aggregated with other proteins such as fibrin, and short repeated hydrophobic elastin sequences have been polymerized into high molecular weight material. The MFUs of the present invention can be used in a similar manner to create fibers for use in making prosthesis consisting essentially of MFUs. For example, MFUs can be co-aggregated with fibrin and other short, hydrophobic elastin sequences and polymerized into higher molecular weight material.

The present invention also provides MFUs modeled on animal elastin. Such MFUs are useful, for example, in elastic materials. The amino acid sequences of several animal elastins are known, including mouse, rat, chicken bovine and porcine.

The present invention also relates to MFUs modeled on other fibrous, self-assembling proteins, including but not limited to lamprin and spider silk proteins. The MFUs of these proteins contain sufficient information (i.e., sufficient beta-sheet/beta-turn structures) to direct their alignment into fibrillar polymeric structures. For example, the amino acid sequence of lamprin is known, and the secondary structure of this protein is believed to comprise a number of beta-sheet/beta-turn structures. Robson et al., supra. An MFU modeled on lamprin in accordance with the present invention comprises a portion of the amino acid sequence of lamprin that has at least three beta-sheet/beta-turn structures, and which is not the naturally occurring lamprin protein. In a preferred embodiment, an MFU modeled on lamprin consists essentially of a portion of the amino acid sequence of lamprin. Alternatively, an MFU modeled on lamprin comprises a portion of the amino acid sequence of lamprin, wherein the amino acid sequence is modified by one or more additions, substitutions and/or deletions, as described above.

MFUs modeled on lamprin and other fibrous proteins can be used to make a variety of materials. The materials have the special properties of high tensile strength, elasticity and plasticity of their parent proteins, and thus are suitable for a number of different applications, for example, in cords and ropes for use in parachutes, which require high tensile strength.

The present invention also encompasses materials that include two or more MFUs derived from a single parent protein, wherein the MFUs may be the same or different, and materials which include two or more MFUs derived from different parent proteins. Such combinations of MFUs from the same or different parent proteins can be chosen to form a product with desired physical properties. For example, a combination of an MFU derived from elastin and an MFU derived from a spider silk protein will have the high extensibity of elastin and the high tensile strength of the spider silk protein. Appropriate selection of the MFUs and their relative amounts permits the production of a material with specified properties.

The combination may be in any form, such as a mixture of MFUs, a fusion protein comprising two or more MFUs, or two or more MFUs chemically linked together. For example, one embodiment of the present invention provides a polypeptide comprising an MFU modeled on elastin, such as animal or human elastin, and an MFU modeled on another fibrous protein, such as lamprin or a spider silk protein. Such a polypeptide can be made by methods known to those skilled in the art, for example, by methods used to make fusion proteins. An MFU comprising exons 21 and 22 of human elastin flanked on both sides by tandem repeat sequences from lamprin has been expressed as a fusion protein. See Example 7 below. In an alternative embodiment, a material is provided which comprises an MFU modeled on animal or human elastin chemically-linked to an MFU modeled on lamprin or a spider silk protein. Such chemically-linked polypeptides can be made by methods known to those skilled in the art. Other combinations of MFUs modeled on the same or different parent proteins also are encompassed by the present invention.

The present invention is further illustrated below by reference to the following examples. The examples are illustrative only, and are not to be construed as limiting the scope of the invention.

EXAMPLE 1

Selection of Minimal Functional Unit-1 (MFU-1) of Human Elastin

As discussed above, the beta-sheet/beta-turn structure of the hydrophobic domains of fibrous proteins such as elastin are believed to play an important role in the self-alignment and self-assembly of the proteins. These structures are focused on for the selection of MFUs.

A specific MFU of human elastin (designated MFU-1) was selected for expression. This MFU is encoded by four exon regions of the human elastin gene: exons 20 (35 amnio acids), 21 (14 amino acids), 23 (19 amino acids) and 24 (53 amino acids). FIG. 1C. The amino acid residues of this peptide are underlined in FIG. 1B. The MFU comprises two adjacent central cross linking domains flanked on each side by hydrophobic domains. FIG. 1D is a cartoon representation of the hydrophobic and cross linking domains corresponding to MFU-1. The crosslinking domain containing lysine residues, believed to be in an alpha-helical conformation, is represented by the cylinder. The flanking hydrophobic domains are represented as square planes with protruding hydrophobic side chains. These hydrophobic domains each comprise several beta-sheet/beta-turn structural units. This MFU constitutes only approximately one-sixth of the total mass of elastin, and has a size of about 10,000 daltons.

This particular unit was chosen because the flanking hydrophobic exon, exon 24, contains a seven-fold repeat of a PGVGVA (SEQ ID NO:6) sequence which is likely to play a role in elastin alignment and assembly. The importance of this domain is supported by the fact that domains of similar tandem repeats at this site are found in elastins of several species, and by the evidence that synthetic peptides mimicking this hydrophobic repeat sequence self-aggregate to form fibrillar structures. Also, the PGVGVA (SEQ ID NO:6) sequence interacts specifically with an elastin-binding protein, one of the functions of which is to prevent premature intracellular self-aggregation of tropoelastin. Hinek et al., *J. Cell Biol.* 126: 563–73 (1994). This tropoelastin-binding protein has also been shown to inhibit in vitro self-aggregation of solubilized elastin fragments (kappa-elastin). Hinek, *Cell Adhesion & Comm.* 2: 1–9 (1994).

Peptides comprising other hydrophobic domains of human elastin are expected to posses similar abilities to self-assemble and self-align, and are suitable MFUs in accordance with the present invention. For example, peptides comprising amino acid residues 19–160, 188–367 and 607–717 of the human elastin amino acid sequence set forth in FIG. 1B are suitable MFUs.

EXAMPLE 2

Expression of MFU-1 of Human Elastin

Figure 2:
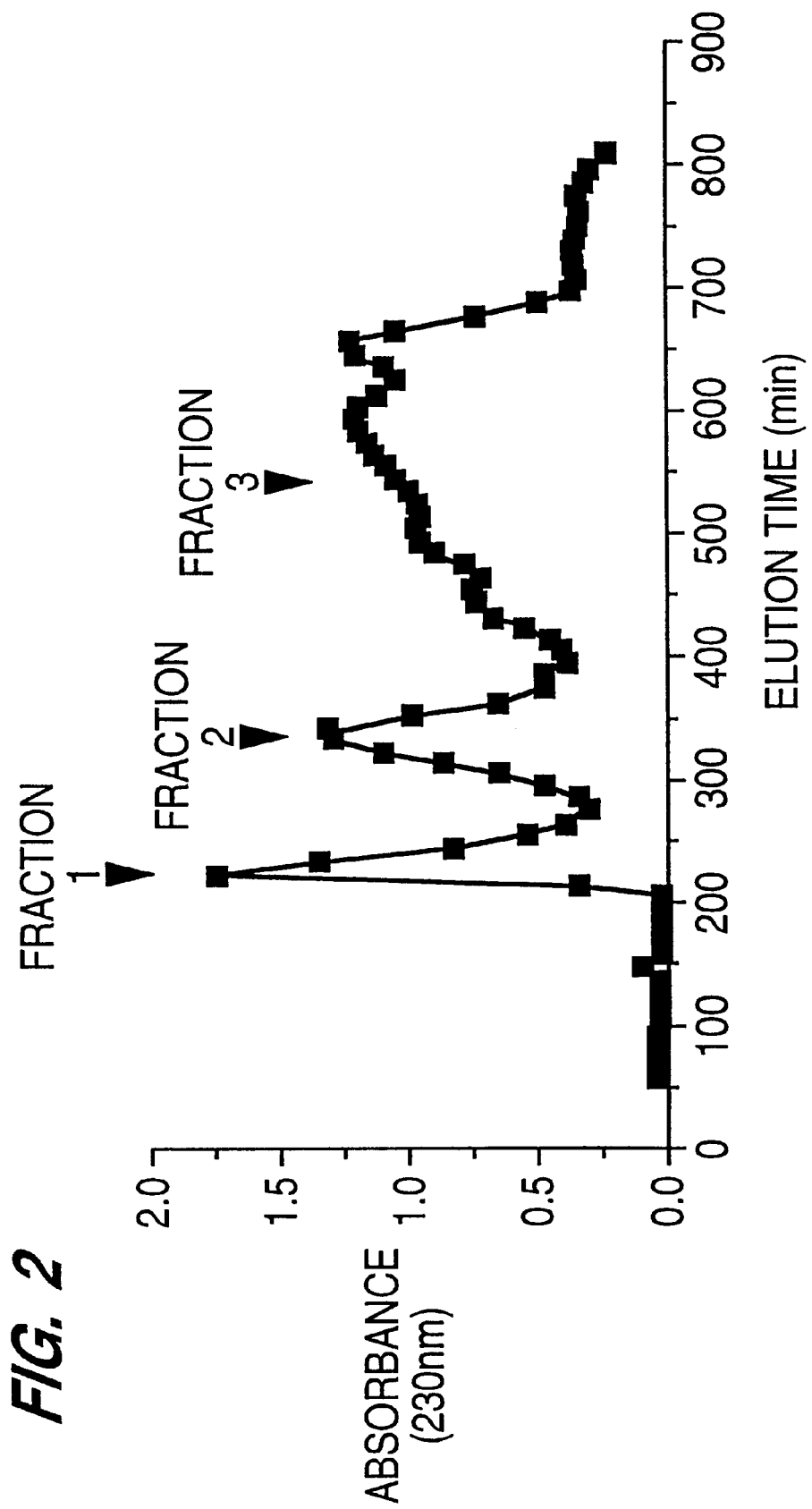
FIG. 2 depicts the chromatography on BioGel P-30 in 0.05M acetic acid of cleavage products after cyanogen bromide treatment to release MFU-1 from the GST fusion protein, as described in Example 2. The MFU-1 is contained in Fraction 1.

By the use of a human fetal aortic elastin cDNA, the region encompassing exons 20, 21, 23, and 24 of human elastin was cloned by PCR. The 5' primer contained a BamHI site, followed by a methionine codon and 15 bases homologous to the 5' end of exon 20. The methionine codon was inserted for subsequent use as a cyanogen bromide cleavage site, since no other methionines occur in the elastin sequence. The 3' primer contained an EcoRI site, followed by a stop codon and 15 bases complementary to the 3' end of exon 24 (see FIG. 1C). The PCR product was ligated into a BamHI-EcoRI digested pGEX-2t vector (Pharmacia) and the sequence confirmed. The ligation product was transfected into *E. coli*. The expressed fusion product was isolated by glutathione affinity chromatography and the elastin MFU cleaved from the GST protein by cyanogen bromide treatment, yielding a ~10 kDa cleavage product. This cleavage product was purified by BioGel P-30 chromatography in 0.05M acetic acid. (FIG. 2). The elastin MFU-1 is contained in Fraction 1.

The identity of the released MFU was confirmed by Western blotting with antibodies to elastin and to the PGVGVA sequence contained in one of the hydrophobic domains, and by amino acid analysis. In particular, Fraction 1 obtained from the BioGel P-30 chromatography depicted in FIG. 2 was characterized by Western Blot analysis. Western blots using a monoclonal antibody to PGVGVA were performed on affinity-purified products before CNBr cleavage and on Fraction 1. A Western blot using a polyclonal antibody to human elastin also was performed on Fraction 1. The yield of the elastin polypeptide is estimated at 1–3 mg/L.

The following table sets forth the amino acid composition of Fraction 1 from chromatography on BioGel P-30. The predicted (expected) and actual (found) compositions are shown.

|     | Expected | Found |
| --- | --- | --- |
| ASP | 0 | 0.7 |
| GLX | 4 | 4.2 |
| HYP | 0 | 0.0 |
| SER | 1 | 1.3 |
| GLY | 33 | 33.8 |
| HIS | 0 | 0.2 |
| ARG | 0 | 0.5 |
| THR | 1 | 1.2 |
| ALA | 27 | 26.9 |
| PRO | 15 | 12.9 |
| TYR | 1 | 1.3 |
| VAL | 25 | 22.3 |
| MET | 0 | 0.3 |
| CYS | 0 | 0.1 |
| ILU | 3 | 3.4 |
| LEU | 1 | 2.4 |
| PHE | 3 | 3.2 |
| LYS | 4 | 5.3 |

Radioactively labelled MFU-1 was generated by conventional means for use in experimentation by incubating the transfected *E. coli* in the presence of radioactively labeled valine and glycine.

EXAMPLE 3

Self-Aggregation of MFU-1 of Human Elastin

While the MFU-1 obtained as described above is soluble at room temperature, the ability of the MFU to self-aggregate (the first step in fiber formation) was readily induced by increasing the salt content of the solution and elevating the temperature, with the onset of coacervation occurring at 53° C. See FIG. 3. This behavior of MFU-1 is similar to the temperature-dependent self-aggregation of the parent molecule, tropoelastin.

EXAMPLE 4

Use of MFU-1 to Humanize Animal-Based Prosthesis

The ability of MFU-1 to coat animal-based prosthetic materials was evaluated as follows:

A matrix of insoluble elastin was prepared from chicken aortic tissue by a cyanogen bromide extraction method. This insoluble, non-human elastin matrix was incubated for 16 hours at 37° in phosphate-buffered saline, at pH 7.4, in the presence of radioactively labeled human MFU-1 prepared as described above. The tissue was then washed extensively with phosphate-buffered saline at pH 7.4.

The association of human elastin MFU-1 with chicken elastin was demonstrated by fluorescence microscopy. Samples of chicken elastin were incubated in the presence of phosphate-buffered saline (PBS) alone and in PBS in the presence of radioactively labeled human elastin MFU-1 (MFU). Increased autofluorescence of elastin after incubation with the human MFU-1 indicated the association of the human MFU-1 with the surface of the chicken elastin. The MFU-1-coated chicken elastin matrix displayed enhanced surface auto-fluorescence which was uniform over the entire surface, suggesting a complete and continuous coating of the matrix by MFU-1.

The following table shows the calculation of the surface coating of chicken elastin with the human elastin MFU-1:

| | Bound MFU (cpm) | Bound MFU (nmoles) | Total Area of Chicken Elastin (mm²) | Total MFU Area (mm²) | MFU Coverage |
|---|---|---|---|---|---|
| PBS | 0 | 0.00 | 13.0 | 0 | 0 |
| PBS | 0 | 0.00 | 16.1 | 0 | 0 |
| MFU | 254 | 0.22 | 13.0 | 3708 | 285 |
| MFU | 147 | 0.13 | 6.7 | 2151 | 321 |

Estimation of surface coverage assumed a cross-sectional diameter of the human MFU-1 of 6 nm. It was estimated that about 1–3 µg of human MFU-1 per mg chicken elastin matrix remained firmly associated with the insoluble matrix of chicken elastin. This amount of MFU-1 is sufficient to cover the estimated surface area of the chicken elastin matrix up to two hundred-fold, and indicates that the MFU-1 formed a multi-layer coating on the chicken elastin matrix.

EXAMPLE 5

Coating Non-Biological Prosthetic Materials With MFU-1 of Human Elastin

The suitability of MFU-1 as a coating material was evaluated for non-biological prosthetic materials, including dacron, polyurethane and teflon.

Via techniques similar to those described in Example 4 above, exposure of non-biological prosthetic materials, including dacron, polyurethane, expanded polytetrafluoroethylene (ePTFE) (Gortex) or a Teflon-coated metal to soluble MFU-1 was shown to result in the coating of these materials with a surface layer of the human elastin MFU. For the Dacron, polyurethane and ePTFE coatings, the amount of bound MFU was sufficient to cover the material at least twenty-fold, based on the surface area of the material and the estimated cross-sectional area of MFU-1. For the teflon-coated metal, the surface coverage was estimated to be approximately 500-fold:

| | Bound MFU (cpm) | Bound MFU (nmoles) | Total Area of Substrate (mm²) | Total MFU Area (mm²) | MFU Coverage |
|---|---|---|---|---|---|
| PBS | 0 | 0.00 | 13.0 | 0 | 0 |
| Polyurethane | 32 | 0.03 | 13.0 | 472 | 36 |
| Dacron | 68 | 0.06 | 13.0 | 989 | 76 |
| Teflon | 87 | 0.08 | 14.0 | 1276 | 91 |
| Teflon-Coated Metal | 102 | 0.04 | 1.19 | 706 | 572 |

The formation of multiple layers of MFUs on these materials indicates that, once an initial layer of MFU forms on the prosthetic material, additional layers are formed by self-aggregation of the MFUs.

MFUs bound in this manner are not readily removed by washing. The coating can be made permanent by treating the material to crosslink the MFUs covalently to the prosthetic material, via methods previously described (for example, in U.S. Pat. No. 4,474,851 (Urry), supra), and by crosslinking the MFUs to each other via their amino groups. This provides a permanent elastin matrix on the surface of the prosthesis.

Because elastin is inherently non-thrombogenic, coating these synthetic prostheses with human elastin MFUs reduces the tendency of prostheses made from these materials to bind and activate platelets. For example, we have demonstrated that ePTFE materials coated with MFU-1 do not exhibit platelet adherence or activation.

We also have demonstrated that materials coated with human elastin MFUs provide a surface for cell attachment and growth. In particular, vascular smooth muscle cells and endothelial cells were found to adhere, spread, and proliferate on surfaces coated with MFU-1. Similar results are expected with materials formed from human elastin MFUs.

EXAMPLE 6

Expression of MFU-2 of Human Elastin

Via techniques similar to those described in Example 2 above, a second polypeptide modeled on human elastin (MFU-2) has been expressed and partially characterized. This polypeptide comprises a tandem duplicate of MFU-1, consisting of exons 20, 21, 23, 24, 21, 23, and 24. FIGS. 4A, 4C. It contains three hydrophobic domains and two crosslinking domains. FIG. 4B. MFU-2 undergoes coacervation at approximately 34° C., indicating an increased tendency for self-aggregation compared to MFU-1. This increased tendency arises from the duplication of hydrophobic and crosslinking domains.

EXAMPLE 7

Expression of MFUs Based on Lamprin and Elastin/Lamprin

Via techniques similar to those described in Example 2 above, constructs consisting of the entire polypeptide sequence of lamprin were expressed. A chimeric construct consisting of a crosslinking domain of human elastin (exons 21 and 23) flanked on both sides by tandem repeat sequences from lamprin, (GGLGY)6(SEQ ID NO:8), also was expressed.

EXAMPLE 8

Formation of Fibrillar Matrices From MFUs and Their Use as a Prosthetic Material MFUs can be used to produce fibrillar matrices useful, for example, for making prosthetic materials. This can be effected either during the process of self-aggregation or after self-aggregation, by extrusion into an appropriate medium or by other known procedures for making fibers. Self-assembly of MFU-1 into fibrillar structures similar to those formed by human tropoelastin can be confirmed by transmission electron microscopy of the coacervates.

Polypeptides comprising multiple repeats of MFUs or comprising a region of human elastin containing two or more MFUs, up to and including the entire tropoelastin molecule, also can be used to make fibers in accordance with the present invention. The larger MFU-containing peptides may demonstrate improved self-assembly or fiber-forming characteristics, or may produce fibers with superior mechanical properties.

Once formed, the fibrillar matrices can be stabilized by crosslinking either enzymatically (for example, with lysyl oxidase) or chemically (via bi-functional aldehydes or other crosslinking agents) to produce material similar to natural elastin. Coacervation-generated polymers of MFU-1 have been stabilized by chemical crosslinking of lysine residue side chains via a catechol/peroxidase method described in Stahmann et al., *Biopolymers* 16: 1307–18 (1977). The ability to stabilize the polymers by this method confirms that the process of self-aggregation (coacervation) aligns the lysine residues appropriately for crosslinking.

The MFUs also can be co-aggregated and co-crosslinked with other human proteins, such as collagens, to more closely mimic natural structural materials.

Material made from MFU fibers can be formed or woven into sheets or tubes for various prosthetic uses. This human-like material has superior biocompatibility compared to other elastin-containing materials heretofore proposed for prostheses.

It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. A polypeptide that comprises a minimal functioning unit, wherein said minimal forming unit is present in SEQ ID NO:1 and is comprised of (i) at least three beta-sheet/beta-turn structures and at least one amino acid residue that participates in cross-linking, and (ii) is not a naturally occurring fibrous protein.

2. The polypeptide of claim 1, wherein said minimal function unit is modified by the addition, deletion or substitution of from 1 to about 10 amino acid residues.

3. The polypeptide of claim 1, wherein said polypeptide comprises an amino acid sequence selected from the group of sequences consisting of amino acid residues 374–499 of SEQ ID NO:1, said sequence set forth in SEQ ID NO:9, said sequence set forth in SEQ ID NO:10, and said sequence set forth in SEQ ID NO:11.

4. The polypeptide of claim 1, wherein said polypeptide comprises an amino acid sequence selected from the group of sequences consisting of amino acid residues 374–499 of SEQ ID NO:1, said sequence set forth in SEQ ID NO:9, said sequence set forth in SEQ ID NO:10, and said sequence set forth in SEQ ID NO:11, wherein said sequence is modified by the addition, deletion or substitution of from 1 to about 10 amino acid residues.

5. The polypeptide of claim 1, wherein said minimal function unit comprises an amino acid sequence selected from the group consisting of amino acid residues 374–499, 19–160, 188–367, and 607–717 of SEQ ID NO:1.

6. A prosthesis comprising said polypeptide of claim 1.

7. The prosthesis of claim 6, wherein said minimal function unit is modified by the addition, deletion or substitution of from 1 to about 10 amino acid residues.

8. The prosthesis of claim 6, wherein said polypeptide comprises an amino acid sequence selected from the group of sequences consisting of amino acid residues 374–499 of SEQ ID NO:1, said sequence set forth in SEQ ID NO:9, said sequence set forth in SEQ ID NO:10, and said sequence set forth in SEQ ID NO:11.

9. The prosthesis of claim 6, wherein said polypeptide comprises an amino acid sequence selected from the group of sequences consisting of amino acid residues 374–499 of SEQ ID NO:1, said sequence set forth in SEQ ID NO:9, said sequence set forth in SEQ ID NO:10, and said sequence set forth in SEQ ID NO:11, wherein said sequence is modified by the addition, deletion or substitution of from 1 to about 10 amino acid residues.

10. The prosthesis of claim 6, wherein said prosthesis is selected from the group consisting of prostheses for blood vessel replacement, prostheses for heart valve replacement, prostheses for tissue replacement, prostheses for covering burns, prostheses for covering wounds, and stents.

11. The prosthesis of claim 6, wherein said minimal functioning unit comprises an amino acid sequence selected from the group consisting of amino acid residues 374–499, 19–160, 188–367, and 607–717 of SEQ ID NO:1.

12. The prosthesis of claim 6, wherein said prosthesis comprises a material selected from the group consisting of animal material, synthetic material and metal, and wherein a surface of the material is coated with said polypeptide.

13. The prosthesis of claim 12, wherein said polypeptide comprises an amino acid sequence selected from the group of sequences consisting of amino acid residues 374–499 of SEQ ID NO:1, said sequence set forth in SEQ ID NO:9, said sequence set forth in SEQ ID NO:10, and said sequence set forth in SEQ ID NO:11.

* * * * *

SEQUENCE LISTING

<160> NUMBER OF SEQ ID NOS: 11

<210> SEQ ID NO 1
<211> LENGTH: 731
<212> TYPE: PRT
<213> ORGANISM: Homo sapiens

<400> SEQUENCE: 1

```
Gly Gly Val Pro Gly Ala Ile Pro Gly Gly Val Pro Gly Gly Val Phe
  1               5                  10                  15

Tyr Pro Gly Ala Gly Leu Gly Ala Leu Gly Gly Gly Ala Leu Gly Pro
             20                  25                  30

Gly Gly Lys Pro Leu Lys Pro Val Pro Gly Gly Leu Ala Gly Ala Gly
         35                  40                  45

Leu Gly Ala Gly Leu Gly Ala Phe Pro Ala Val Thr Phe Pro Gly Ala
     50                  55                  60

Leu Val Pro Gly Gly Val Ala Asp Ala Ala Ala Ala Tyr Lys Ala Ala
 65                  70                  75                  80

Lys Ala Gly Ala Gly Leu Gly Gly Val Pro Gly Val Gly Gly Leu Gly
                 85                  90                  95

Val Ser Ala Gly Ala Val Val Pro Gln Pro Gly Ala Gly Val Lys Pro
            100                 105                 110

Gly Lys Val Pro Gly Val Gly Leu Pro Gly Val Tyr Pro Gly Gly Val
            115                 120                 125

Leu Pro Gly Ala Arg Phe Pro Gly Val Gly Val Leu Pro Gly Val Pro
        130                 135                 140

Thr Gly Ala Gly Val Lys Pro Lys Ala Pro Gly Val Gly Gly Ala Phe
145                 150                 155                 160

Ala Gly Ile Pro Gly Val Gly Pro Phe Gly Gly Pro Gln Pro Gly Val
                165                 170                 175

Pro Leu Gly Tyr Pro Ile Lys Ala Pro Lys Leu Pro Gly Gly Tyr Gly
            180                 185                 190

Leu Pro Tyr Thr Thr Gly Lys Leu Pro Tyr Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Lys Ala Ala
        275                 280                 285
```

```
Lys Tyr Gly Ala Ala Ala Gly Leu Val Pro Gly Gly Pro Gly Phe Gly
    290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Ala Lys Ala Ala Ala
                340                 345                 350

Lys Ala Ala Lys Tyr Gly Ala Arg Pro Gly Val Gly Val Gly Gly Ile
            355                 360                 365

Pro Thr Tyr Gly Val Gly Ala Gly Gly Phe Pro Gly Phe Gly Val Gly
    370                 375                 380

Val Gly Gly Ile Pro Gly Val Ala Gly Val Pro Gly Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Val Gly Thr Pro Ala
            420                 425                 430

Ala Ala Ala Lys Ala Ala Ala Lys Ala Ala Gln Phe Gly Leu Val
            435                 440                 445

Pro Gly Val Gly Val Ala Pro Gly Val Gly Val Ala Pro Gly Val Gly
    450                 455                 460

Val Ala Pro Gly Val Gly Leu Ala Pro Gly Val Gly Val Ala Pro Gly
465                 470                 475                 480

Val Gly Val Ala Pro Gly Val Gly Val Ala Pro Ala Ile Gly Pro Gly
                485                 490                 495

Gly Val Ala Ala Ala Lys Ser Ala Ala Lys Val Ala Ala Lys Ala
            500                 505                 510

Gln Leu Arg Ala Ala Gly Leu Gly Ala Gly Ile Pro Gly Leu Gly
        515                 520                 525

Val Gly Val Gly Val Pro Gly Leu Gly Val Gly Ala Gly Val Pro Gly
    530                 535                 540

Leu Gly Val Gly Ala Gly Val Pro Gly Phe Gly Ala Gly Ala Asp Glu
545                 550                 555                 560

Gly Val Arg Arg Ser Leu Ser Pro Glu Leu Arg Glu Gly Asp Pro Ser
                565                 570                 575

Ser Ser Gln His Leu Pro Ser Thr Pro Ser Ser Pro Arg Val Pro Gly
            580                 585                 590

Ala Leu Ala Ala Ala Lys Ala Ala Lys Tyr Gly Ala Ala Val Pro Gly
        595                 600                 605

Val Leu Gly Gly Leu Gly Ala Leu Gly Gly Val Gly Ile Pro Gly Gly
    610                 615                 620

Val Val Gly Ala Gly Pro Ala Ala Ala Ala Ala Ala Lys Ala Ala
625                 630                 635                 640

Ala Lys Ala Ala Gln Phe Gly Leu Val Gly Ala Ala Gly Leu Gly Gly
                645                 650                 655

Leu Gly Val Gly Gly Leu Gly Val Pro Gly Val Gly Gly Leu Gly Gly
                660                 665                 670

Ile Pro Pro Ala Ala Ala Ala Lys Ala Ala Lys Tyr Gly Ala Ala Gly
            675                 680                 685

Leu Gly Gly Val Leu Gly Gly Ala Gly Gln Phe Pro Leu Gly Gly Val
        690                 695                 700

Ala Ala Arg Pro Gly Phe Gly Leu Ser Pro Ile Phe Pro Gly Gly Ala
```

```
                705                 710                 715                 720
        Cys Leu Gly Lys Ala Cys Gly Arg Lys Arg Lys
                        725                 730
```

```
<210> SEQ ID NO 2
<211> LENGTH: 200
<212> TYPE: PRT
<213> ORGANISM: Artificial Sequence
<220> FEATURE:
<223> OTHER INFORMATION: Description of Artificial Sequence: Synthetic
      MFU-1 polypeptide

<400> SEQUENCE: 2

Phe Pro Gly Phe Gly Val Gly Gly Ile Pro Gly Val Ala Gly
  1               5                  10                  15

Val Pro Gly Val Gly Gly Val Pro Gly Val Gly Gly Val Pro Gly Val
                 20                  25                  30

Gly Ile Ser Pro Glu Ala Gln Ala Ala Ala Ala Lys Ala Ala Lys
             35                  40                  45

Tyr Gly Val Gly Thr Pro Ala Ala Ala Ala Lys Ala Ala Lys
 50                  55                  60

Ala Ala Gln Phe Gly Leu Val Pro Gly Val Gly Val Ala Pro Gly Val
 65                  70                  75                  80

Gly Val Ala Pro Gly Val Gly Val Ala Pro Gly Val Gly Leu Ala Pro
                 85                  90                  95

Gly Val Gly Val Ala Pro Gly Val Gly Val Ala Pro Gly Val Gly Val
                100                 105                 110

Ala Pro Ala Ile Gly Pro Glu Ala Gln Ala Ala Ala Ala Lys Ala
                115                 120                 125

Ala Lys Tyr Gly Val Gly Thr Pro Ala Ala Ala Ala Lys Ala Ala
                130                 135                 140

Ala Lys Ala Ala Gln Phe Gly Leu Val Pro Gly Val Gly Val Ala Pro
145                 150                 155                 160

Gly Val Gly Val Ala Pro Gly Val Gly Val Ala Pro Gly Val Gly Leu
                165                 170                 175

Ala Pro Gly Val Gly Val Ala Pro Gly Val Gly Val Ala Pro Gly Val
                180                 185                 190

Gly Val Ala Pro Ala Ile Gly Pro
                195                 200
```

```
<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Ala Lys
  1
```

```
<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Lys Ala Ala Ala Lys
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Gly Val Gly Val Ala
 1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Pro Gly Val Gly
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Pro Gly Gly
 1

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Leu Gly Tyr Gly Gly Leu Gly Tyr Gly Gly Leu Gly Tyr Gly
 1               5                  10                  15

Gly Leu Gly Tyr Gly Gly Leu Gly Tyr Gly Gly Leu Gly Tyr
                20                  25                  30

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      MFU-3 polypeptide

<400> SEQUENCE: 9

Pro Gly Phe Gly Val Gly Val Gly Gly Ile Pro Gly Val Ala Gly Val
 1               5                  10                  15

Pro Gly Val Gly Gly Val Pro Gly Val Gly Val Pro Gly Val Gly
                20                  25                  30

```
Ile Ser Pro Glu Ala Gln Ala Ala Ala Lys Ala Ala Lys Tyr
         35                  40                  45

Gly Val Gly Thr Pro Ala Ala Ala Ala Lys Ala Ala Lys Ala
 50                  55                  60

Ala Gln Phe Gly Leu Val Pro Gly Val Gly Val Ala Pro Val Gly
 65                  70                  75                  80

Val Ala Pro Gly Val Gly Val Ala Pro Gly Val Gly Leu Ala Pro Gly
                 85                  90                  95

Val Gly Val Ala Pro Gly Val Gly Val Ala Pro Gly Val Gly Val Ala
             100                 105                 110

Pro Ala Ile Gly Pro
        115

<210> SEQ ID NO 10
<211> LENGTH: 118
<212> TYPE: PRT
<213> ORGANISM: Artificial Sequence
<220> FEATURE:
<223> OTHER INFORMATION: Description of Artificial Sequence: Synthetic
      MFU-4 polypeptide

<400> SEQUENCE: 10

Phe Pro Gly Phe Gly Val Gly Val Gly Gly Ile Pro Gly Val Ala Gly
 1               5                  10                  15

Val Pro Gly Val Gly Gly Val Pro Gly Val Gly Gly Val Pro Gly Val
                 20                  25                  30

Gly Ile Ser Pro Glu Ala Gln Ala Ala Ala Ala Lys Ala Ala Lys
             35                  40                  45

Tyr Gly Val Gly Thr Pro Ala Ala Ala Ala Lys Ala Ala Ala Lys
 50                  55                  60

Ala Ala Gln Phe Gly Leu Val Pro Gly Val Gly Val Ala Pro Gly Val
 65                  70                  75                  80

Gly Val Ala Pro Gly Val Gly Val Ala Pro Gly Val Gly Leu Ala Pro
                 85                  90                  95

Gly Val Gly Val Ala Pro Gly Val Gly Val Ala Pro Gly Val Gly Val
             100                 105                 110

Ala Pro Ala Ile Gly Pro
        115

<210> SEQ ID NO 11
<211> LENGTH: 199
<212> TYPE: PRT
<213> ORGANISM: Artificial Sequence
<220> FEATURE:
<223> OTHER INFORMATION: Description of Artificial Sequence: Synthetic
      MFU-5 polypeptide

<400> SEQUENCE: 11

Pro Gly Phe Gly Val Gly Val Gly Gly Ile Pro Gly Val Ala Gly Val
 1               5                  10                  15

Pro Gly Val Gly Gly Val Pro Gly Val Gly Gly Val Pro Gly Val Gly
                 20                  25                  30

Ile Ser Pro Glu Ala Gln Ala Ala Ala Ala Lys Ala Ala Lys Tyr
             35                  40                  45

Gly Val Gly Thr Pro Ala Ala Ala Ala Lys Ala Ala Lys Ala
 50                  55                  60

Ala Gln Phe Gly Leu Val Pro Gly Val Gly Val Ala Pro Gly Val Gly
 65                  70                  75                  80
```

```
                                    -continued

Val Ala Pro Gly Val Gly Val Ala Pro Gly Val Gly Leu Ala Pro Gly
            85                  90                  95

Val Gly Val Ala Pro Gly Val Gly Val Ala Pro Gly Val Gly Val Ala
            100                 105                 110

Pro Ala Ile Gly Pro Glu Ala Gln Ala Ala Ala Ala Ala Lys Ala Ala
            115                 120                 125

Lys Tyr Gly Val Gly Thr Pro Ala Ala Ala Ala Ala Lys Ala Ala Ala
            130                 135                 140

Lys Ala Ala Gln Phe Gly Leu Val Pro Gly Val Gly Val Ala Pro Gly
145                 150                 155                 160

Val Gly Val Ala Pro Gly Val Gly Val Ala Pro Gly Val Gly Leu Ala
            165                 170                 175

Pro Gly Val Gly Val Ala Pro Gly Val Gly Val Ala Pro Gly Val Gly
            180                 185                 190

Val Ala Pro Ala Ile Gly Pro
            195
```